United States Patent
Kim

(10) Patent No.: US 7,824,182 B2
(45) Date of Patent: Nov. 2, 2010

(54) DENTAL FILING TOOL

(76) Inventor: Daniel S. Kim, 217 SE. 136th Ave., Suite 101, Vancouver, WA (US) 98684

(*) Notice: Subject to any disclaimer, the term of this patent is extended or adjusted under 35 U.S.C. 154(b) by 36 days.

(21) Appl. No.: 12/284,087

(22) Filed: Sep. 17, 2008

(65) Prior Publication Data

US 2009/0253096 A1 Oct. 8, 2009

Related U.S. Application Data

(63) Continuation-in-part of application No. 11/401,538, filed on Apr. 10, 2006, now abandoned, which is a continuation-in-part of application No. 10/945,033, filed on Sep. 21, 2004, now abandoned, application No. 12/284,087, which is a continuation-in-part of application No. 11/982,117, filed on Nov. 1, 2007, which is a continuation-in-part of application No. 10/945,033, application No. 11/271,291, filed on Nov. 12, 2005.

(51) Int. Cl.
*A61C 3/06* (2006.01)
(52) U.S. Cl. .................................................. 433/142
(58) Field of Classification Search .................. 433/142, 433/148, 149; 132/321, 329
See application file for complete search history.

(56) References Cited

U.S. PATENT DOCUMENTS

| | | | |
|---|---|---|---|
| 788,947 A | 5/1905 | Roth | |
| 1,201,875 A | 10/1916 | Russ | |
| 2,148,734 A | 2/1939 | Du Jat | |
| 2,288,011 A | 6/1942 | Mizzzy | |
| 2,702,555 A | 2/1955 | De Mar | |
| 2,730,804 A | 1/1956 | Saupe | |
| 2,736,327 A * | 2/1956 | Schlicksupp | 132/323 |
| 2,771,085 A * | 11/1956 | Fleming | 132/321 |
| 3,411,723 A | 11/1968 | Kohn | |
| 3,624,908 A | 12/1971 | Ricketts et al. | |
| 4,030,198 A | 6/1977 | Gerber | |
| 4,592,729 A | 6/1986 | Bilciurescu | |
| 4,738,621 A * | 4/1988 | Lowder | 433/142 |
| 5,084,978 A | 2/1992 | McReynolds | |
| 6,386,837 B2 | 5/2002 | Blank | |
| 6,386,873 B1 * | 5/2002 | Blank | 433/142 |
| 6,508,649 B2 | 1/2003 | Gratz | |
| 6,766,808 B2 | 7/2004 | Gwen | |
| 7,455,521 B2 * | 11/2008 | Fishburne, Jr. | 433/142 |

(Continued)

FOREIGN PATENT DOCUMENTS

JP  7-194618  *  8/1995

*Primary Examiner*—Ralph A Lewis
(74) *Attorney, Agent, or Firm*—Mark E. Beatty; Rylander & Associates PC

(57) ABSTRACT

A dental filing tool includes a handle and a filing strip, wherein the handle includes first and second handle parts, each having a bridge and corresponding first and second arms extending therefrom, the handle parts connectable by a plurality of snap fittings and forming finger pads at either end when snapped together. Male snap fittings may include one or more cross-slots extending at least part of the length of the male snap fitting. A filing strip includes abrasive material on one or both faces, or a sharp-edged perforation pattern, and one or more serrated edges. The interior surfaces of the handle may be beveled to improve comfort and better fit between teeth. The bridge portion of the handle parts can include a raised portion and indicia formed into or printed on the raised portion.

15 Claims, 8 Drawing Sheets

U.S. PATENT DOCUMENTS

| | | |
|---|---|---|
| 2005/0271999 A1 | 12/2005 | Fishburne, Jr. |
| 2006/0057540 A1* | 3/2006 | Navarro ...................... 433/166 |
| 2006/0183075 A1 | 3/2006 | Kim |
| 2006/0093991 A1 | 5/2006 | Kim |
| 2006/0127845 A1* | 6/2006 | Khouri ....................... 433/142 |
| 2006/0063131 A1 | 8/2006 | Kim |

* cited by examiner

DENTAL FILING TOOL

CROSS-REFERENCES TO RELATED APPLICATION

This application is a continuation-in-part of and claims priority to U.S. application Ser. No. 11/401,538, filed Apr. 10, 2006, now abandoned and U.S. application Ser. No. 11/982,117, filed Nov. 1, 2007. Application Ser. No. 11/401,538 is a continuation-in-part of, and claims priority to, nonprovisional patent application Ser. No. 10/945,033 filed Sep. 21, 2004 now abandoned. Application Ser. No. 11/982,117 is a continuation-in-part of application Ser. No. 10/945,033, filed Sep. 21, 2004, now abandoned and application Ser. No. 11/271,291, filed Nov. 12, 2005, and application Ser. No. 29/285,421, filed Mar. 28, 2007. All of the listed applications are hereby incorporated by reference into this application.

FIELD OF THE INVENTION

The present invention relates to disposable dental filing tools for filing interproximal regions.

BACKGROUND

This invention relates to disposable dental filing tools, more particularly to a snap-together dental filing tool that holds a thin filing strip provided with abrasive material or sharp cutting edges for efficient filing of the interproximal area and fitting of dental crowns, bridges, onlays, inlays and fillings.

The current conventional method for fitting dental crowns, bridges, onlays and inlays, herein referred to generally as restorations, involves the dental practitioner sliding colored carbon paper, of which the thickness is the recommended measured distance between teeth, between the interproximal area of the tooth and the restoration. The carbon paper marks with carbon ink the proximal contact area where the two surfaces of the teeth and/or restoration are too close, and then the practitioner grinds the restoration with a rotary instrument to remove excess material. This method is tedious, inefficient, and inexact. The dental practitioner has to continually remove the restoration and grind the heavy proximal contact surface until the fitting surface and shape is achieved, at which point the restoration may be permanently fixed. It is a time consuming process and there is possibility of over-grinding, in which case a new restoration must be reconstructed to replace it. This involves significant expense of time and money, not to mention inconvenience for the patient who suffers for the delay and agony.

Another method employed is the stand alone use of a metal filing strip coated with some superfine abrasive material. The metal filing strip is inserted between the interproximal area to file down the proximal contact area of the crown for an accurate fit. Since the space between the tooth and the crown, bridge, onlay, and inlay must not be too close nor too spaced apart the practitioner must file incrementally. These steps are repeated until the desired distance between the tooth and the restoration is achieved. Because the filing strip is extremely thin, narrow, and malleable, it is necessary for the practitioner to hold the strip taut at opposite ends with fingers from both hands. Unfortunately holding the filing strip in such as manner is cumbersome in the patient's mouth and impedes the practitioner from achieving desired angles and restricts range of motion to effectively file. Especially when the patient is receiving crowns, bridges, onlays, or inlays in the back of the mouth where it is considerably more difficult to access, it is difficult for the practitioner to file since both hands are needed to hold keep in the strip and often a patient's mouth is too small or cannot open wide enough to accommodate the file comfortably. As a result, the patient must endure strenuous stretching of the lips and jaw area. Often a practitioner struggles to find the best placement for fingers to pinch the strip to create sufficient tension while attempting to minimize the restricting presence of both hands in the patient's mouth. This method is inefficient, tiresome for the practitioner, and uncomfortable for the patient. Moreover, because of the difficulty involved handling the filing strip, often patients sustain suffer small cuts due to the sharp edges of the strip coming in contact with gums and lips while filing the tooth or restoration.

Another method employed is that a thin metal strip coated with fine abrasive material is fastened to a removable bow which is attached to a handle. Generally, the bow and handle are too long to maneuver in the mouth and limit the size of abrasive strip, which is the actual working surface, and yields ineffective results in the mouth for posterior teeth. Replacing the filing strip after each use is also a hassle for the dental staff due to the fact that disassembly and assembly involve extremely small fasteners and tools. The bow handle is designed to be re-used and so is too expensive to simply dispose of. Compression on the ends of the bows will tend to loosen and pop off removable filing strips.

In order to solve the existing problems with the current methods for interproximal grinding and adjustment between restorations and teeth, it is the object of the present invention to provide an inexpensive tool which has a body that secures a filing strip securely enough which can be held by one hand between opposable fingers. This allows for the practitioner to maneuver within the patient's mouth with easier reach and greater range of motion for more time efficient and effective filing and grinding of the interproximal area with greater comfort for the patient for a quicker fitting of crowns, bridges, onlays, and inlays.

In addition to these inefficiencies many areas of the world lack high technology powered dental equipment and extensive training for dentists and dental assistants. Thus, the process of using powered tools to shape restorations out of the mouth are often not available, and such dentists are in need of an inexpensive, safe and reliable means of filing restorations and fillings in-situ.

A number of devices have provided abrasive surfaces for filing crowns, but lack the safety, control and ease of manufacture of the present invention. None of the known body of art, taken either singularly or in combination, is seen to describe the instant invention as claimed.

U.S. Pat. No. 6,386,873 to Blank teaches a filing tool with a Y-shaped handle with bosses on the ends to hold a filing blade, which is mounted by squeezing together the handle ends to hang the blade on the bosses through mounting holes. Blank does not teach an inexpensive, disposable, snap-together system with positive capture of a filing strip. Blank teaches a device which purports to be ergonomic for the user, which is an improvement to a degree. However, the user has to grasp the Blank device at the prongs in order to exert sufficient lateral force to be useful. Grasping Blank at the prongs would naturally tend to compress them together, creating a serious danger that the blade would separate because it lacks a positive capture feature. In addition, comparing the handle length required to form the Y-shape and provide the extended portion intended for gripping (see Blank, FIG. 1, #22), the Blank apparatus is actually quite large and clumsy for use inside a patient's mouth.

U.S. Pat. No. 2,730,804 to Saupe teaches a dental filing tool which uses a replaceable filing blade which slides into a jointed holder. The filing blade is gripped only along one side and not held in tension in the axis of the working surface. This limits the amount of lateral pressure which can be applied, and creates a danger where if the filing blade was used in a tight-fitting area the blade would either displace or bend. Saupe does not teach tapering and rounding the inner edges of the blade holder to allow the blade handle to fit comfortably against the gap between teeth without causing damage. Saupe does not teach apparatus having a positive capture feature for a filing strip.

Japan Patent 593138377 (the JP '377 patent) teaches a dental filing tool with a U-shaped handle and filing strip. However, JP '377 teaches a replaceable filing strip mounted on pegs or bosses, without a positive capture feature (see JP '377, FIGS. 3 and 7, #7). There is therefore a significant danger that the blade could separate during use in a patient's mouth. Applying lateral or longitudinal pressure during use naturally causes the user to squeeze the handle together which would loosen the blade and likely cause it to pop off. In addition, if the filing strip hit a difficult or tight area there is substantial risk that it might simply deform and tear off the pegs. This danger could be lessened by angling the pegs (#7) away from each other, but this would make assembly by dental staff very difficult, especially considering the small size of the parts. Nor does JP '377 disclose tapered inner edges to better fit within the facial and lingual embrasures between adjacent teeth, nor integral fingerpads for gripping.

Filing tools with positive capture snap-together assembly are required, where the filing strips are held firmly in place with latching mechanical interference snaps so as to avoid danger of separation due to poorly designed or poorly assembled blade retention means. Injection mold manufacturing techniques reduce cost sufficiently that the dental filing tools may be considered disposable. Disposing of the tools for recycling of the plastic and metal, rather than requiring dental staff to disassemble and replace abrasive strips, saves significant labor and supervision burdens, and prevents mistakes in re-assembly from causing harm to patients. The present invention solves these problems.

Thus, while the foregoing body of art indicates it to be well known to have a dental filing tool, the known art does not teach or suggest a dental filing tool which has the following combination of desirable features: (1) small enough to be held between two fingers by the user; (2) able to hold a filing strip securely without risk of separating in a patient's mouth; (3) inexpensively produced so as to be essentially disposable; (4) allows for easy and effective disinfection; (5) allows for easy and simplified labeling and indexing of filing blades; (6) provides tapered inner edges for comfortable fit into the facial and lingual embrasures; and, (7) provides integral fingerpads for easier control and efficient manufacture.

SUMMARY AND ADVANTAGES

A dental filing tool includes a handle and a filing strip, wherein the handle includes first and second handle parts, each of said first and second handle parts including a bridge having first and second ends, and corresponding first and second arms extending perpendicular from the bridge ends to respective terminal ends, each of the first and second handle parts further including a plurality of corresponding male and female snap fittings located at least at the first and second arm terminal ends and the bridge; and wherein the filing strip includes top and bottom edges, first and second ends, and first and second mounting holes located proximal to the first and second filing strip ends, respectively, for receiving the first and second handle part terminal end snap fittings there through when the first and second handle parts are snapped together.

A dental filing tool includes male snap fittings having a cross-slot extending at least part of the length of the male snap fitting. A dental filing tool includes each of said male snap fittings having first and second intersecting cross-slots extending at least part of the length of the male snap fitting. A dental filing tool includes wherein each of the female snap fittings has a cavity extending into the corresponding handle part and an interior ridge protruding partially into the cavity, and, wherein each of the male snap fittings includes a slotted post extending from the corresponding handle part, from a post base to a post terminal end, the slotted post having an interference ridge protruding from the post and an open slot extending from the post terminal end to a depth distal from the post terminal end, and wherein, the male snap fitting interference ridge engages the female snap interior ridge when a corresponding male snap fitting and female snap fitting are snapped together. A dental filing tool includes the first and second handle parts forming flattened fingerpad rests when snapped together. A dental filing tool includes corresponding first and second arms tapering in thickness to form a beveled interior surface when the first and second handle parts are snapped together. A dental filing tool includes a filing strip coated with abrasive material on at least one surface. A dental filing tool includes a filing strip having sharp-edged perforations. A dental filing tool includes a filing strip having serrated edges along at least one of the top and bottom edges. A dental filing tool includes a filing strip having serrated edges along both of the top and bottom edges. A dental filing tool includes having each of the handle first and second portions include a raised flat portion along the bridge. A dental filing tool includes at least one flat portion provided with indicia.

A dental filing tool a filing strip selected from the group of materials consisting of stainless steel and titanium. A dental filing tool includes a filing strip thickness is in the range 0.04 mm to 0.12 mm (0.0016 to 0.0047 inches). A dental filing tool includes abrasive material coating on at least one surface of the filing strip with diamond dust in the range of 200 grit to 900 grit. A dental filing tool includes a filing strip having a pattern of perforations distributed along the length of said strip. A dental filing tool includes round perforations. A dental filing tool includes diamond-shaped perforations. A dental filing tool includes rectangular perforations. A dental filing tool includes a perforation pattern having alternating groupings of round and diamond-shaped perforations. A dental filing tool includes a perforation pattern having a combination of one or more perforation shapes selected from the group consisting of round, diamond and rectangular. A dental filing tool includes perforations overlapping in the range of one-third to two-thirds. A dental filing tool includes a filing strip coated with abrasive on at least one side.

A dental filing tool as described herein provides the following advantages: (1) small enough to be held between two fingers by the user; (2) able to hold a filing strip securely without risk of separating in a patient's mouth; (3) inexpensively produced so as to be essentially disposable; (4) allows for easy and effective disinfection; (5) allows for easy and simplified labeling and indexing of filing blades; (6) provides tapered inner edges for comfortable fit into the facial and lingual embrasures; and, (7) provides integral fingerpads for easier control and efficient manufacture.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

DETAILED DESCRIPTION

Figure 1:
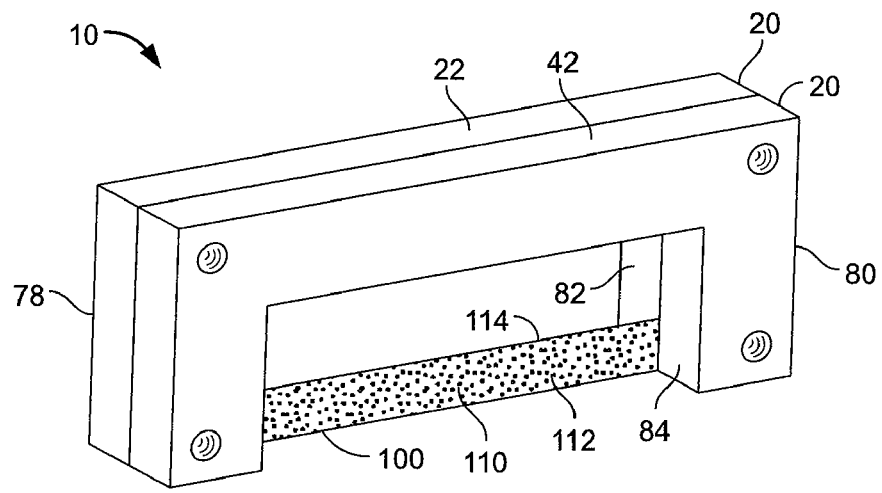
FIG. 1 shows a perspective view of a first embodiment.
Figure 2:
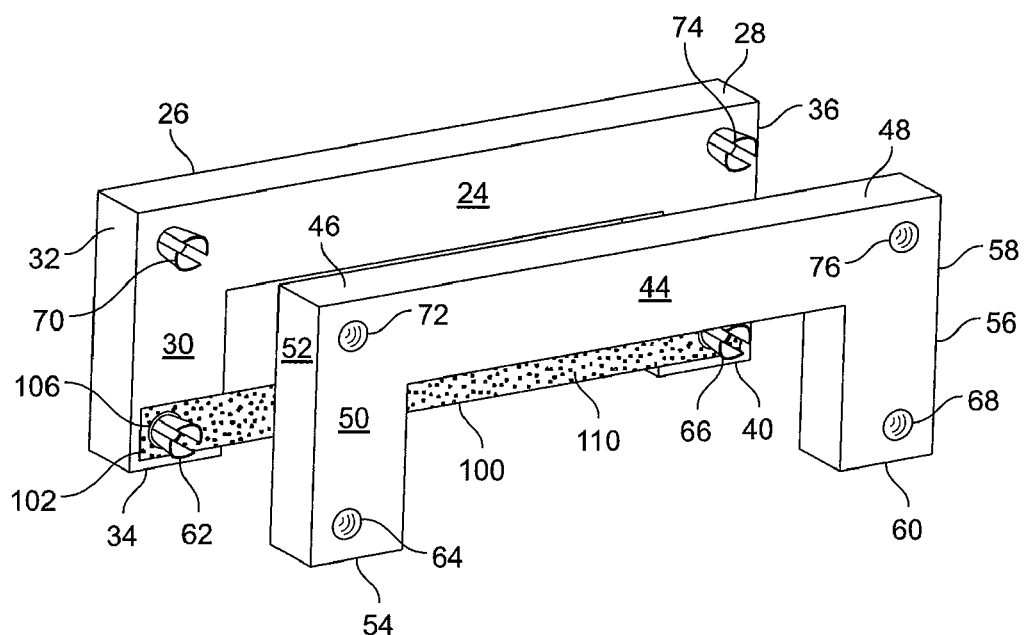
FIG. 2 shows a perspective view of a first embodiment of two components before engagement.
Figure 3:
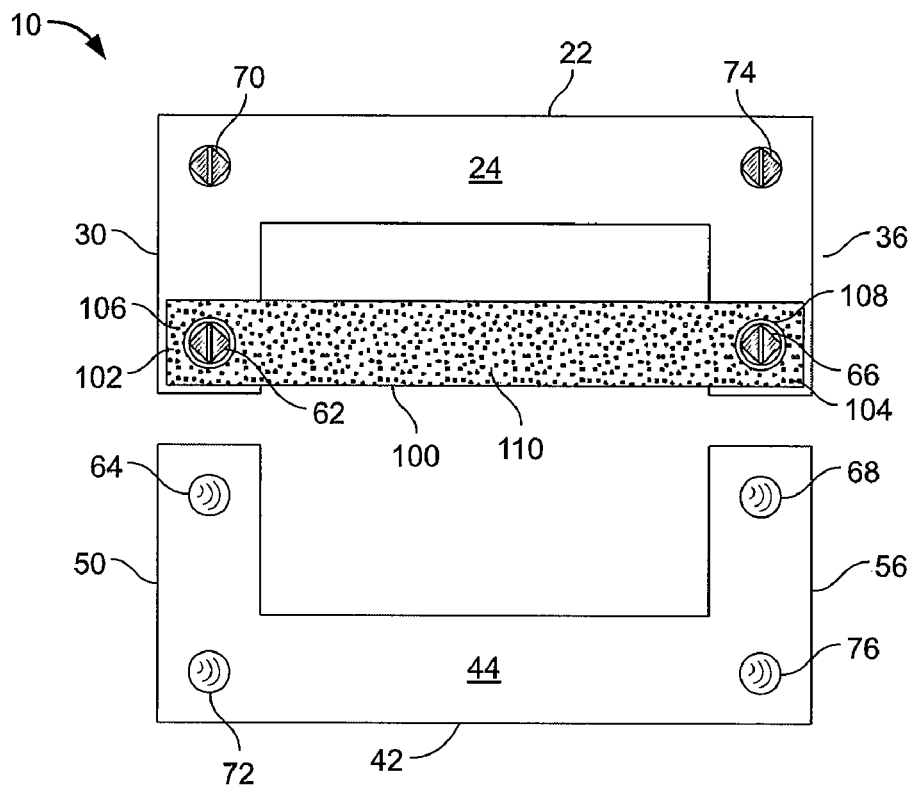
FIG. 3 shows an inside-out view of a first embodiment before engagement.

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

A dental filing tool, comprising a handle and a filing strip, said handle including first and second handle parts, each of said first and second handle parts including a bridge having first and second ends, and corresponding first and second arms extending perpendicular from said bridge ends to respective terminal ends; wherein, each of said first and second handle parts further includes a plurality of corresponding male and female snap fittings located at least at said first and second arm terminal ends and said bridge; and, said filing strip including first and second ends, and first and second mounting holes located proximal to said first and second filing strip ends, respectively, for receiving said first and second handle part terminal end snap fittings there through when said first and second handle parts are snapped together.

Referring to FIGS. 1-3 and 7, a first embodiment of a dental filing tool 10 is shown, having a handle 20 and a filing strip 100. Handle 20 includes first handle part 22 and second handle part 42, which snap together to engage filing strip 100 and create a unitary dental filing tool 10. First handle part 22 includes bridge 24 having first end 26 and second end 28, with first arm 30 extending perpendicular from first end 26 at its base 32 to terminal end 34, and second arm 36 extending perpendicular from second end 28 at its base 38 to terminal end 40. Second handle part 42 includes structures corresponding to first handle part 22. Second handle part 42 includes bridge 44 having first end 46 and second end 48, with first arm 50 extending perpendicular from first end 46 at its base 52 to terminal end 54, and second arm 56 extending perpendicular from second end 48 at its base 58 to terminal end 60. When first and second handle parts 22 and 42 are joined to form handle 20, the outside surfaces 78 and 80 form fingerpads for gripping dental filing tool 10.

First and second handle parts 22 and 42 include a plurality of corresponding male and female snap fittings 62 & 64, 66 & 68, 70 & 72, and 74 & 76. Snap fittings 62 and 64 are located proximal to first and second handle part first arm terminal ends 34 and 54, respectively. Snap fittings 66 and 68 are located proximal to first and second handle part second arm terminal ends 40 and 60, respectively. Snap fittings 70 and 72 are located at first and second handle part bridge first ends 26 and 46, respectively. Snap fittings 74 and 76 are located at first and second handle part bridge second ends 28 and 48, respectively. First and second handle parts 22 and 42 include corresponding snap fittings at least at their respective first and second arm terminal ends 34 & 54 and 40 & 60, in order to positively engage filing strip 100, and on their respective bridges 24 and 44, to provide stability. Preferably snap fittings are provide at the respective bridge first and second ends 26 & 46 and 28 & 48, for stability and strength. More snap fittings may be provided as well.

In the first embodiment all male snap fittings are located on first handle part 22 and corresponding female snap fittings are located on second handle part 42. However, the snap fittings could be arranged with each handle part 22 and 42 including some male snap fittings and some female snap fittings. In the first embodiment, male snap fittings 62, 66, 70 and 74 each include a post with a head of greater cross-section than the post in order to engage the corresponding cavities of female snap fittings 64, 68, 72 and 76. Female snap fittings 64, 68, 72 and 76 may be provides as cavities which do not extend completely through handle second part 42. Alternatively, female snap fittings 64, 68, 72 and 76 may penetrate completely through handle second part 42, and male snap fittings 62, 66, 70 and 74 may include posts of sufficient length to pass completely through female snap fittings 64, 68, 72 and 76 so as to protrude past the outer wall and engage the outside of handle second part 42.

Filing strip 100 includes first end 102 and second end 104, with first mounting hole 106 proximal to first end 102 and second mounting hole 108 proximal to second end 104. Filing strip mounting holes 106 and 108 receive snap fittings 62 &

64 and 66 & 68, respectively. The snap fittings pass through mounting holes 106 and 108 such that the snap fittings act as mounting posts and first and second handle parts 22 and 42 firmly sandwich filing strip 100 between them when snapped together. Filing strip 100 includes abrasive coating 110. Abrasive coating 110 may be present on the front surface 112, or both the front and back surfaces 112 and 114, respectively, of filing strip 100. Abrasive coating 110 may be composed of applied grit, such as diamond dust in the range 200 to 900 grit, which is adhered to a surface 112 and/or 114, or an equivalent roughness patterned surface treatment pressed into or imposed on surface 112 and/or 114, such as a roughened steel surface. Filing strip 100 is preferably in the range of 0.04 mm to 0.12 mm thick (0.0016 to 0.0047 inches). Sets of filing strips 100 may be provided in varying thicknesses within the desired range to allow a user to select the most suitable thickness as required.

Figure 4:
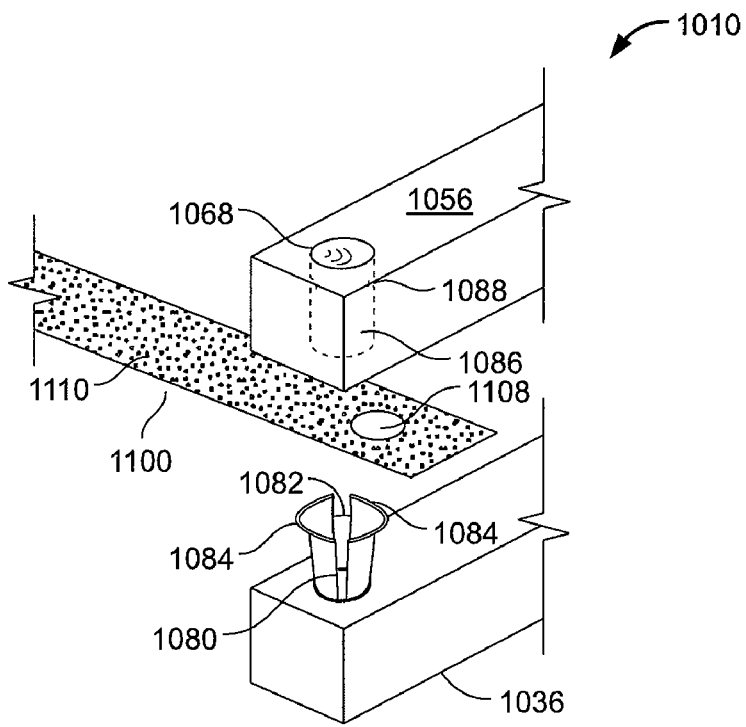
FIG. 4 shows a partially exploded close up view of a second embodiment.

Referring to FIG. 4, a second embodiment of a dental filing tool 1010 is shown, similar to the described first embodiment but including an alternative snap fitting. In a second embodiment 1010, male snap fitting 1066 includes a post projection 1080, interference ridge 1084 protruding from post projection 1080 to form an interference snap head, and cross-slot 1082 extending at least part of the length of the male snap fitting 106. Referring to FIG. 4, in a second embodiment cross-slot 1082 extends the entire length of male snap fitting 106. Female snap fitting 1068 includes cavity 1086 extending into second handle part second arm 1056, and interior ridge 1088 protruding partially into cavity 1086 for engaging male snap fitting interference ridge 1084.

Figure 5:
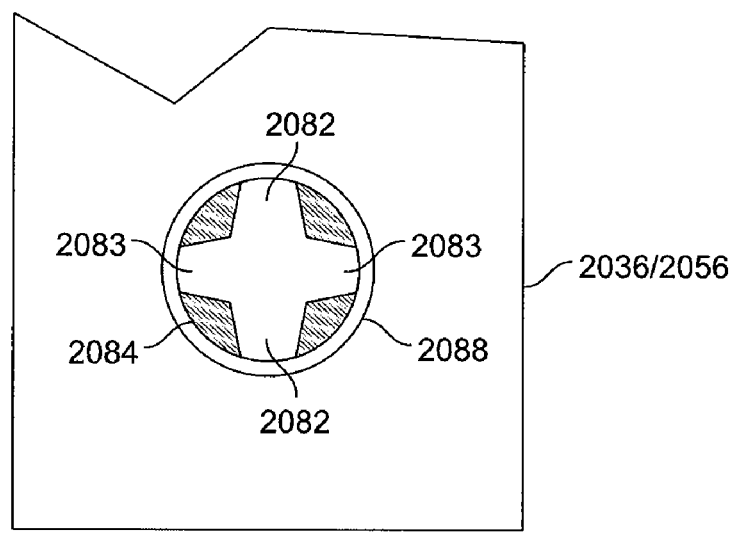
FIG. 5 shows an end on close up view of an inserted snap fitting of a third embodiment.
Figure 6:
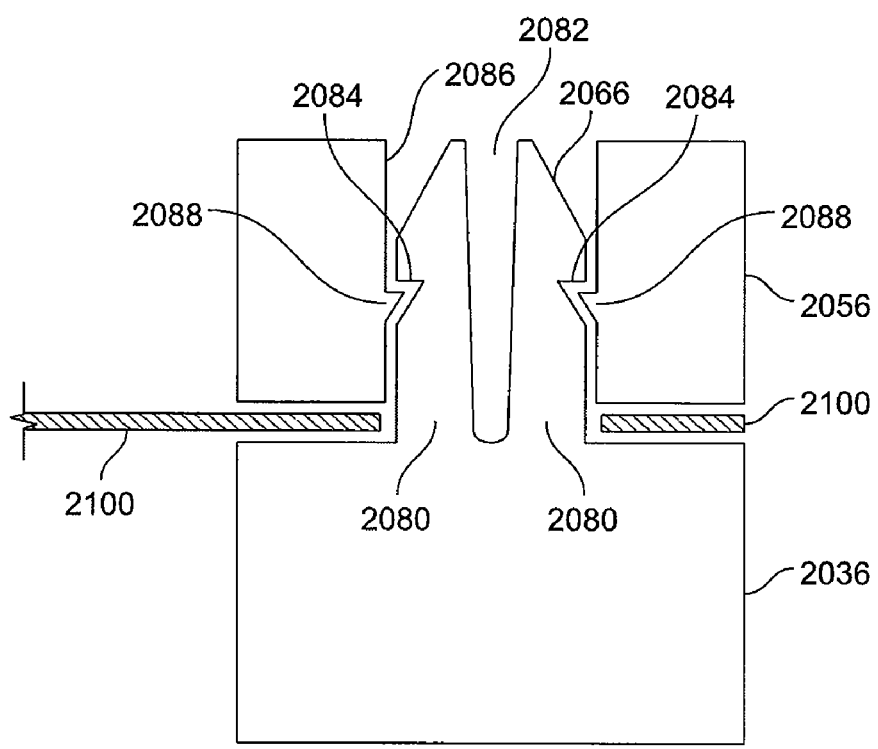
FIG. 6 shows a cut-away view of an inserted snap fitting of a third embodiment.
Figure 7:
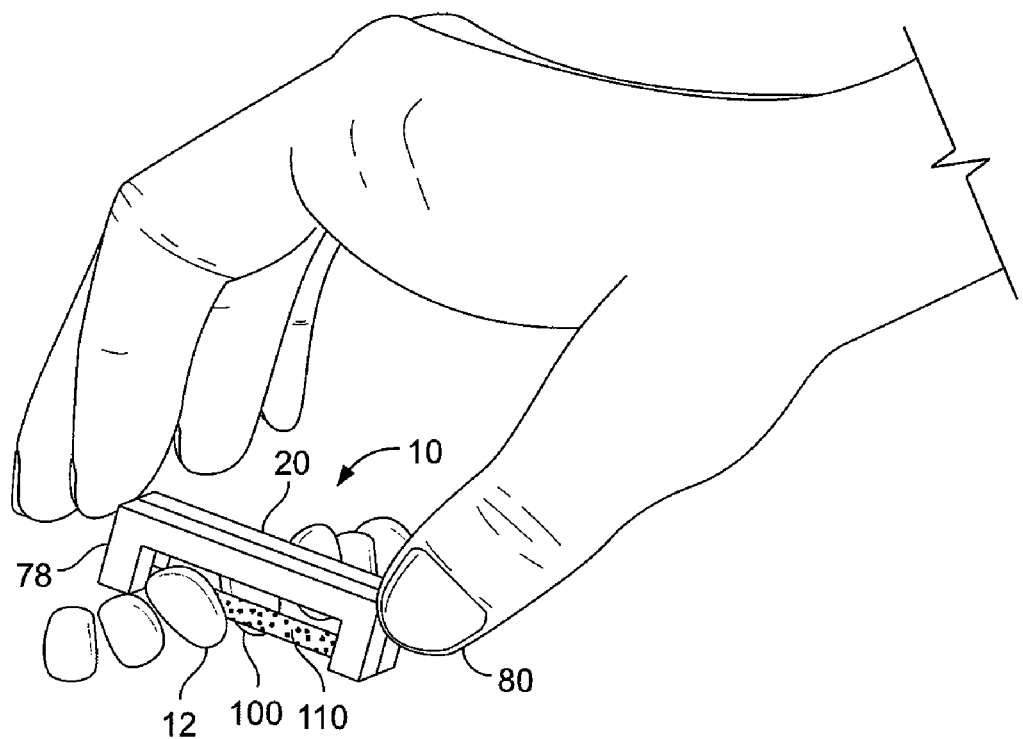
FIG. 7 shows the insertion of a dental filing tool interproximally.

Referring to FIGS. 5 and 6, a third embodiment of a dental filing tool 2010 is shown, including a male snap fitting having intersecting cross-slots 2082 and 2083. Post projection 2080 extends outward from arm terminal end 2036. Interference ridge 2084 protrudes from post projection 2080 to form an interference snap head. The thickness of the base of post projection 2080 proximal to arm terminal end 2036 may be increased so as to increase the spring strength and fatigue life of post projection 1080. In this third embodiment the thickness of the base of post projection 2080 is approximately equal to cross-section diameter of interference ridge 2084. Female snap fitting cavity 2086, extending into arm terminal end 2056, includes interior ridge 2088 protruding partially into the cavity 2086 for engaging male snap fitting interference ridge 2084. Filing strip 2100 is sandwiched between arm terminal ends 2036 and 2056.

In this specification, the term "cross-slot" refers to a slot that extends entirely across the cross-section of a male snap fitting, such that the terminal ends of the male snap fitting can compress together when passing through a restricted passage but will spring back after clearing the restriction. Cross-slots allow male snap fittings to compress while passing through female snap fitting cavities, especially those including a protruding interior ridge, and then spring back out when past the constriction in order to engage the female snap fitting. This prevents damage to the interference ridges on the male snap fittings caused by forcing non-compressible male snap fittings through, and thereby reduces the danger that snap fittings will separate during use.

Figure 8:
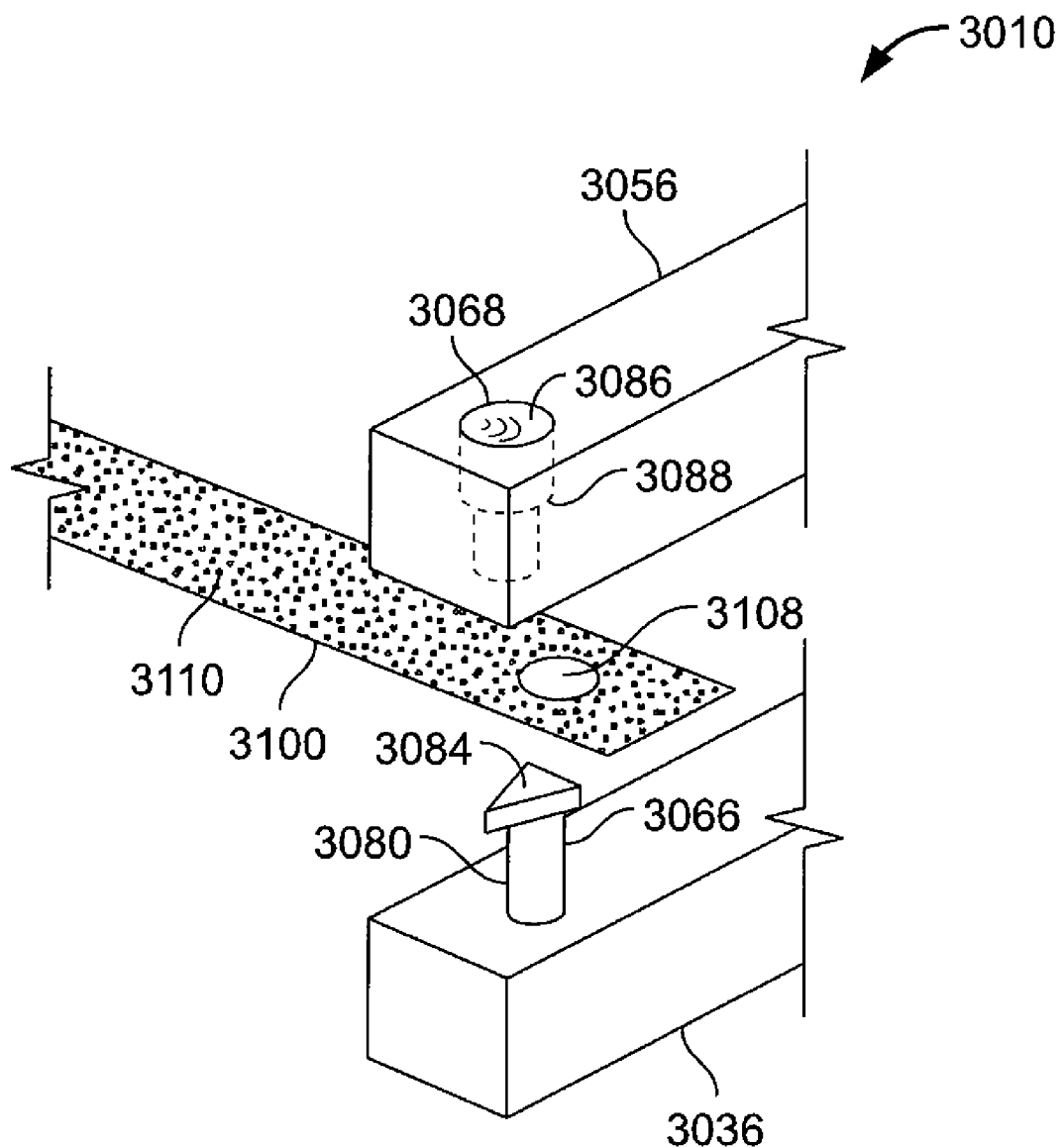
FIG. 8 shows a partially exploded close up view of a fourth embodiment.

Referring to FIG. 8, a fourth embodiment of a dental filing tool 3010 is shown, similar to other described embodiments, but including an alternative solid snap fitting. Male snap fitting 3066 includes a post projection 3080, and interference ridge 3084 protruding from post projection 3080 to form an interference snap head. Female snap fitting 1068 includes cavity 3086 extending into second handle part second arm 3056, and interior ridge 3088 protruding partially into cavity 3086 for engaging male snap fitting interference ridge 3084.

Figure 9:
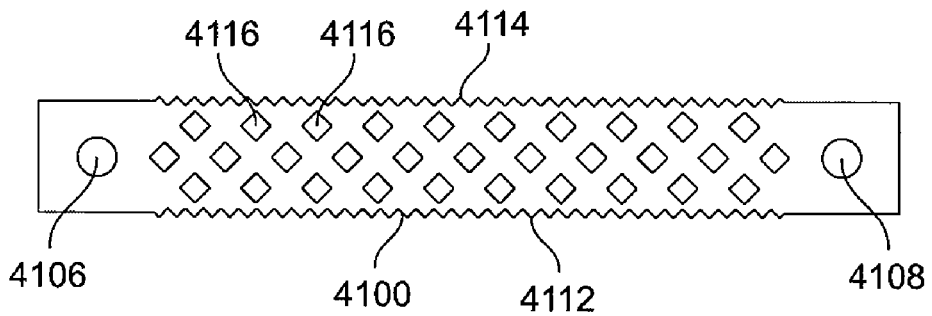
FIG. 9 shows an alternative filing strip.
Figure 10:
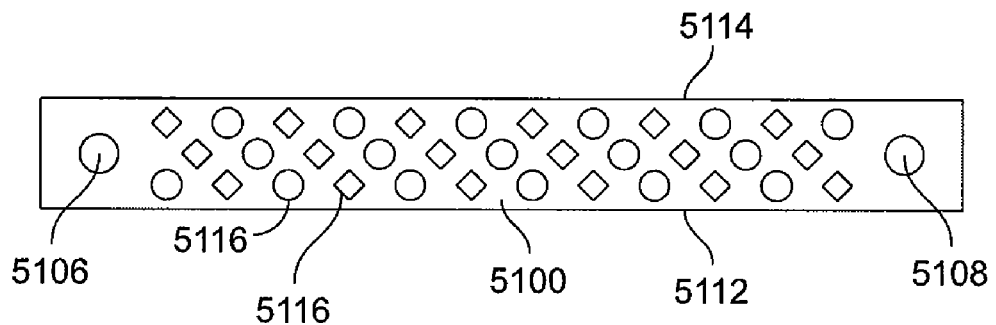
FIG. 10 shows an alternative filing strip.
Figure 11:
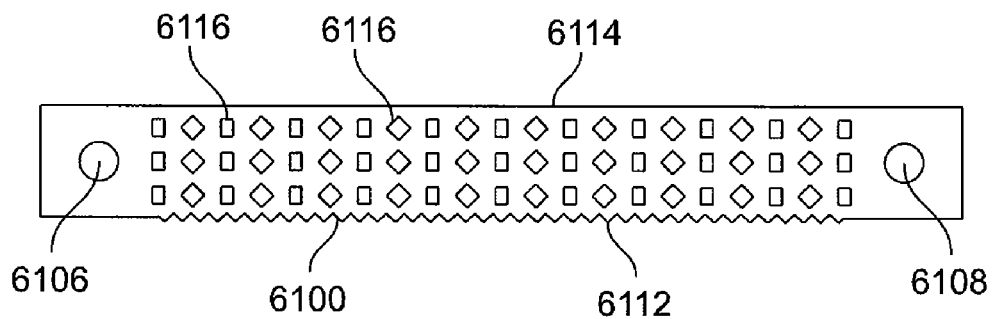
FIG. 11 shows an alternative filing strip.

Referring to FIGS. 9-11, alternative embodiments of filing strips 4100, 5100, and 6100 are provided, which are mechanically interchangeable. Referring to FIG. 9, filing strip 4100 includes first and second ends 4102 and 4104, respectively, with mounting holes 4106 and 4108 proximal to first and second ends 4102 and 4104. Bottom edge 4112 and top edge 4114 are provided with serrations, to provide cutting capability in both upward and downward directions. Diamond-shaped perforations 4116 are provided for abrasion/material removal. As filing strip 4100 moves back and forth or up and down over a surface, perforations 4116 act as a multitude of cutting/scraping edges for removing material. The use of perforations 4116 eliminates the need for abrasive coatings on filing strips, such as diamond dust, which can create additional residual debris in a patient's mouth which may be unhealthy for the patient. Preferably the perforations overlap in orientation to prevent development of ridges on the target surface.

Referring to FIG. 10, filing strip 5100 includes first and second ends 5102 and 5104, respectively, with mounting holes 5106 and 5108 proximal to first and second ends 5102 and 5104. Bottom edge 5112 and top edge 5114 are not provided with serrations. A mixed pattern of diamond-shaped perforations and round or oval perforations 5116 are provided for abrasion/material removal. As filing strip 5100 moves back and forth or up and down over a surface, perforations 5116 act as a multitude of cutting/scraping edges for removing material. Varying the shape of perforations 5116 presents varying cutting edge angles to a target surface to improve effect on surfaces with randomly oriented surface incongruities. The use of perforations 5116 eliminates the need for abrasive coatings on filing strips, such as diamond dust, which can create additional residual debris in a patient's mouth which may be unhealthy for the patient.

Referring to FIG. 11, filing strip 6100 includes first and second ends 6102 and 6104, respectively, with mounting holes 6106 and 6108 proximal to first and second ends 6102 and 6104. Bottom edge 6112 and top edge 6114 are provided with serrations, to provide cutting capability in both upward, and downward directions. A mixed pattern of diamond-shaped perforations and rectangular perforations 6116 is provided for abrasion/material removal. As filing strip 6100 moves back and forth or up and down over a surface, perforations 6116 act as a multitude of cutting/scraping edges for removing material. Varying the shape of perforations 6116 presents varying cutting edge angles to a target surface to improve effect on surfaces with randomly oriented surface incongruities. The use of perforations 6116 eliminates the need for abrasive coatings on filing strips, such as diamond dust, which can create additional residual debris in a patient's mouth which may be unhealthy for the patient.

Perforations 4116, 5116 and 6116 may be through cutouts, or may be indentations pressed or formed into the surface of file strips 4100, 5100 and 6100. Cutout patterns may be created by many known methods, such as pressing or punch-and-die systems. File strips are preferably made from tough metal which can be readily sterilized, such as stainless steel or titanium. First and second handle parts are preferably made from plastic to facilitate inexpensive manufacture and easy disposal.

Figure 12:
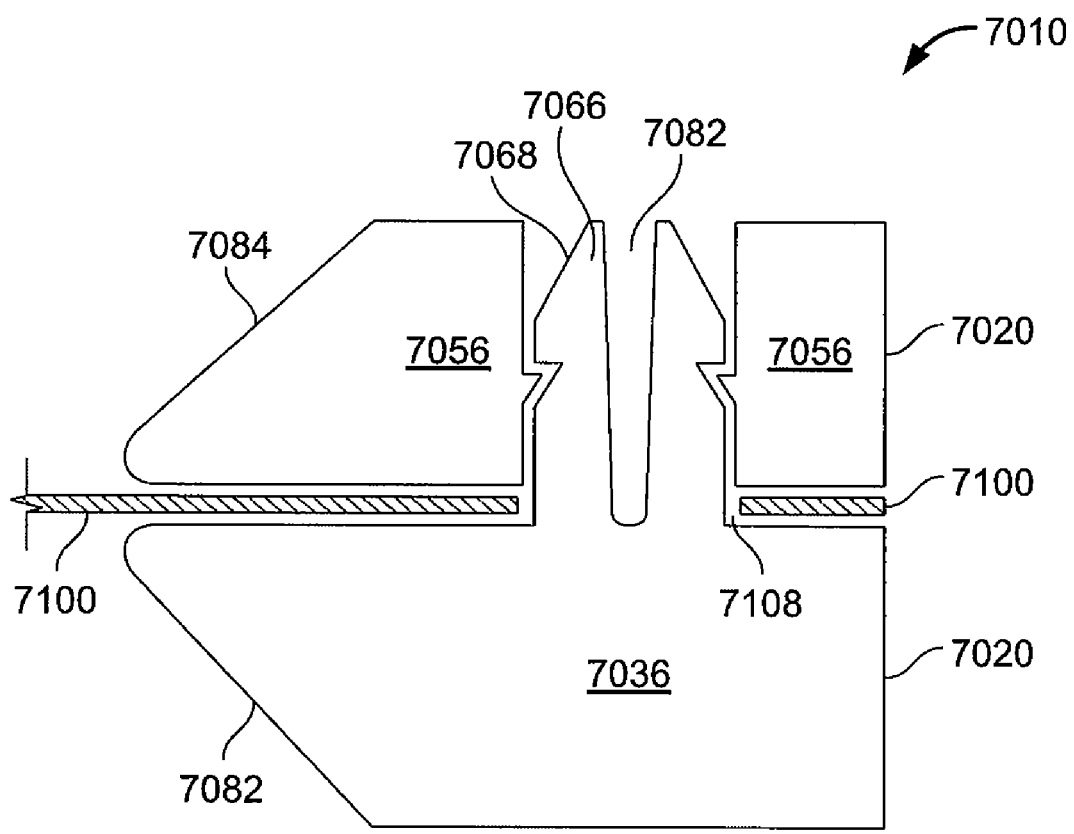
FIG. 12 shows a cut-away view of an inserted snap fitting of a fifth embodiment having beveled interior surfaces.

Referring to FIG. 12, a partial cross-section of a fifth embodiment of a dental filing tool 7010 is shown having beveled interior surfaces 7082 and 7084 to better fit the interproximal areas, thereby permitting a longer back-and-forth stroke. Beveled interior surfaces 7082 and 7084 extend the entire inside perimeter of handle 7020. First and second handle part second arms 7036 and 7056, respectively, are shown in cutaway for orientation. Slotted mail snap fitting 7066, having cross-slot 7082, snaps into female snap fitting 7068 through filing strip mounting hole 7108, so that first and second handle parts positively capture filing strip 7100 and sandwich it between for stability. Beveled surfaces 7082 and 7084 may be radiused for greater patient comfort. The beveling angle of the interior surfaces of handle 7020 provides optimal access to the interproximal area between teeth and/or restorations, but maintains adequate thickness to prevent filing strip 100 from slipping too deep inflicting undesirable cuts, nicks, and other injuries against gums.

Figure 13:
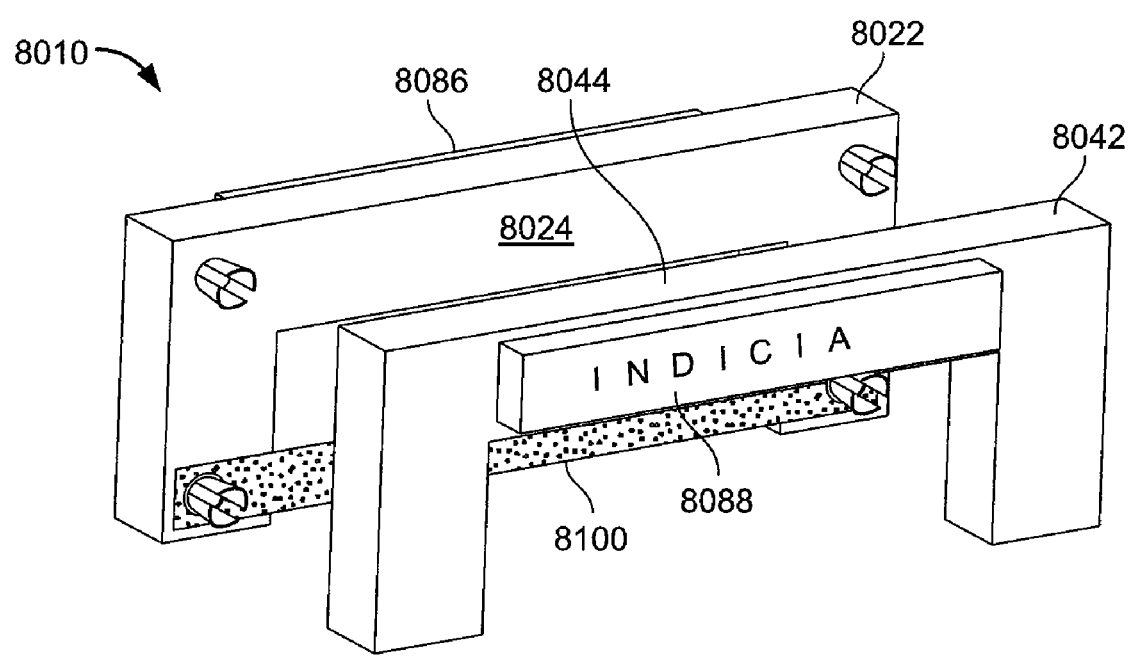
FIG. 13 shows a perspective view of a sixth embodiment of two components before engagement.

Referring to FIG. 13, a sixth embodiment of a dental filing tool 8010 is shown, having first and second handle parts 8022 and 8042, respectively, and filing strip 8100. Raised flat portions 8086 and 8088 are provided along bridge portions 8024 and 8044, respectively, having indicia printed on one or both raised flat portions. Raised flat portions 8086 and 8088 provide added stiffness to bridge portions 8024 and 8044, and provide a convenient location to imprint a logo, part number, or other indicia.

Referring FIGS. 1-3 and 7, in use a dental filing tool 10, is assembled by mounting filing strip 100 over male snap fittings 62 and 66 through mounting holes 106 and 108, then snapping together first and second handle parts 22 and 42, which positively captures filing strip 100 and creates a handle with finger gripping areas at bridge first and second ends 26 & 46 and 28 & 48. The dental filing tool 10 is then gripped between the thumb and forefinger using finger pads 78 and 80 and inserted into the interproximal area 12 to remove material and shape the target in a controlled manner using a back and forth motion. Moreover, it should also be appreciated that handle 20 contains the filing strip 100 within a protective frame shielding the patient from suffering ambient cuts and nicks of the gums, lips, and cheek walls while the user is repositioning, re-angling, or moving the dental filing tool 10 within the mouth. Referring to FIGS. 9 and 11, a dental filing tool is used to saw between teeth, or dental restorations, to cut through material which may have inadvertently sealed between teeth.

Referring again to FIGS. 1-3 and 7, in a first embodiment filing strip 100 is fitted under tension. Filing strip 100 may also be fitted in compression so as to form a bowed curve in use for easily filing rounded interproximal surfaces. Even when filing strip 100 is mounted under tension, the slight malleability of the strip 100 still allows the user to manipulate it with directional pressure applied through the handle 20 to form to any convexities along interproximal surfaces of teeth 12. As the filing tool 10 is pulled back and forth between the area of proximal surface contact the abrasive lateral surface of the filing strip 100 gently removes enamel or restoration material in whatever conservative or aggressive increments desired by the user in relation to the repetitive filing motions and applied pressure.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

I claim:

1. A dental filing tool, comprising a handle and a filing strip, wherein:

said handle includes first and second handle parts, each of said first and second handle parts including a bridge having first and second ends, and corresponding first and second arms extending perpendicular from said bridge ends to respective terminal ends, each of said first and second handle parts further including a plurality of corresponding male and female snap fittings located at least at said first and second arm terminal ends and said bridges; and, said filing strip includes top and bottom edges, first and second ends, and first and second mounting holes located proximal to said first and second filing strip ends, respectively, for receiving said first and second handle part terminal end snap fittings there through when said first and second handle parts are snapped together, and further wherein each of said male snap fittings includes a cross-slot extending at least part of the length of said male snap fitting.

2. A dental filing tool, comprising a handle and a filing strip, wherein:

said handle includes first and second handle parts, each of said first and second handle parts including a bridge having first and second ends, and corresponding first and second arms extending perpendicular from said bridge ends to respective terminal ends, each of said first and second handle parts further including a plurality of corresponding male and female snap fittings located at least at said first and second arm terminal ends and said bridges; and, said filing strip includes top and bottom edges, first and second ends, and first and second mounting holes located proximal to said first and second filing strip ends, respectively, for receiving said first and second handle part terminal end snap fittings there through when said first and second handle parts are snapped together, and further wherein each of said male snap fittings includes first and second intersecting cross-slots extending at least part of the length of said male snap fitting.

3. A dental filing tool, comprising a handle and a filing strip, wherein:

said handle includes first and second handle parts, each of said first and second handle parts including a bridge having first and second ends, and corresponding first and second arms extending perpendicular from said bridge ends to respective terminal ends, each of said first and second handle parts further including a plurality of corresponding male and female snap fittings located at least at said first and second arm terminal ends and said bridges, said filing strip includes top and bottom edges, first and second ends, and first and second mounting holes located proximal to said first and second filing strip ends, respectively, for receiving said first and second handle part terminal end snap fittings there through when said first and second handle parts are snapped together, each of said female snap fittings including a cavity extending into said corresponding handle part and an interior ridge protruding partially into said cavity; and, each of said male snap fittings including a slotted post extending from said handle part from a post base to a post terminal end, said slotted post having an interference ridge proximal to said post terminal end protruding from said post and an open slot extending from said post terminal end to a depth distal from said post terminal end; and, wherein, said male snap fitting interference ridge engages said female snap interior ridge when a corresponding male snap fitting and female snap fitting are snapped together.

4. A dental filing tool as in claims 1, 2 or 3, wherein when said first and second handle parts are snapped together, the corresponding first and second arms form flattened fingerpad rests.

5. A dental filing tool as in claims 1, 2 or 3, wherein said corresponding first and second arms taper in thickness to form a beveled interior surface when said first and second handle parts are snapped together.

6. A dental filing tool as in claims 1, 2 or 3, wherein said filing strip is coated with abrasive material on at least one surface.

7. A dental filing tool as in claims 1, 2 or 3, wherein said filing strip includes serrated edges along at least one of said top and bottom edges.

8. A dental filing tool as in claim 7, wherein said filing strip includes serrated edges along both of said top and bottom edges.

9. A dental filing tool as in claims 1, 2 or 3, wherein each of said handle first and second portions include a raised flat portion along said bridge.

10. A disposable dental filing tool of claim 9, wherein at least one of said raised flat portions is provided with indicia.

11. A dental filing tool as in claims 1, 2 or 3, wherein said filing strip thickness is in the range 0.04 mm to 0.12 mm (0.0016 to 0.0047 inches).

12. A dental filing tool as in claims 1, 2 or 3, wherein said abrasive material comprises coating on at least one surface of said strip with diamond dust in the range of 200 grit to 900 grit.

13. A dental filing tool as in claims 1, 2 or 3, wherein said filing strip includes a pattern of sharp-edged perforations distributed along the length of said strip.

14. A dental filing tool as in claim 13, wherein said perforation pattern comprises a combination of one or more perforation shapes selected from the group consisting of round, diamond and rectangular.

15. A dental filing tool as in claim 13, wherein said perforations overlap in the range of one-third to two-thirds.

* * * * *